(12) United States Patent
Beck et al.

(10) Patent No.: US 10,876,935 B2
(45) Date of Patent: Dec. 29, 2020

(54) SYSTEMS AND METHODS FOR WATER SAMPLING

(71) Applicant: 2NDNATURE Software Inc., Santa Cruz, CA (US)

(72) Inventors: Nicole Beck, Santa Cruz, CA (US); Krista McDonald, Santa Cruz, CA (US); Raph Townsend, Santa Cruz, CA (US); Robb Kraft, Santa Cruz, CA (US)

(73) Assignee: 2NDNature Software Inc., Santa Cruz, CA (US)

( * ) Notice: Subject to any disclaimer, the term of this patent is extended or adjusted under 35 U.S.C. 154(b) by 0 days.

(21) Appl. No.: 16/132,135

(22) Filed: Sep. 14, 2018

(65) Prior Publication Data
US 2020/0088609 A1    Mar. 19, 2020

(51) Int. Cl.
*G01N 1/16* (2006.01)
*G01N 33/18* (2006.01)
*G01N 1/20* (2006.01)

(52) U.S. Cl.
CPC ............ *G01N 1/16* (2013.01); *G01N 1/2035* (2013.01); *G01N 33/18* (2013.01)

(58) Field of Classification Search
CPC ............... G01N 2001/1043; G01N 2021/8405
See application file for complete search history.

(56) References Cited

U.S. PATENT DOCUMENTS

| | | | | |
|---|---|---|---|---|
| 1,780,597 A * | 11/1930 | Mayhall | ............... | G01N 1/12 374/157 |
| 4,442,720 A * | 4/1984 | Apley | ............... | G01N 1/2035 73/863.31 |
| 5,471,886 A * | 12/1995 | Kalidindi | ............... | G01N 1/08 73/864.63 |
| 5,608,171 A | 3/1997 | Hunter et al. | | |
| 5,695,719 A * | 12/1997 | Lynggaard | ............... | B01D 61/28 422/504 |
| 5,783,758 A * | 7/1998 | Dudley | ............... | G01N 1/2035 73/863.52 |
| 5,942,440 A * | 8/1999 | Dooley | ............... | G01N 33/1826 436/125 |
| 8,610,895 B1 * | 12/2013 | Irani | ............... | G01N 33/2823 356/445 |
| 2009/0101555 A1 * | 4/2009 | Scarpine | ............... | C02F 1/004 210/170.03 |

(Continued)

FOREIGN PATENT DOCUMENTS

CN          205317538 U     6/2016

OTHER PUBLICATIONS

"City of Salinas Stormwater Monitoring and Reporting Program—Quality Assurance Project Plan", 2NDNATURE, LLC et al., Dec. 20, 2017, 93 pgs.

(Continued)

*Primary Examiner* — Paul M. West
*Assistant Examiner* — Mark A Shabman
(74) *Attorney, Agent, or Firm* — KPPB LLP (57) ABSTRACT

A water sampling system having multiple collection channels configured to collect multiple samples of a fluid as the fluid flow rate and level changes with respect to time. The system is designed to connect to and sample urban storm water runoff outfalls, pipes and drains.

13 Claims, 9 Drawing Sheets

(56) References Cited

U.S. PATENT DOCUMENTS

2011/0056890 A1* 3/2011 Cobb .................... C02F 1/004
 210/739
2013/0000391 A1* 1/2013 Khuzwayo ............... G01N 1/16
 73/61.59
2018/0251713 A1* 9/2018 Angelescu ............... C12M 1/26

OTHER PUBLICATIONS

"Flow Monitoring Selection Guide", HACH, DOC030.53.10129.Dec17, Dec. 2017, 32 pgs.
"Industrial Stormwater Monitoring and Sampling Guide", U.S. Environmental Protections Agency, EPA 832-B-09-003, Mar. 2009, 51 pgs.
"Isco 5800 Refrigerated Sampler", Isco Product Data, Teledyne Isco, 2012, L-1149, 2 pgs.
"Stormwater Monitoring Guide", Teledyne Isco, 2012, 20 pgs.
"Urban Stormwater BMP Performance Monitoring", A Guidance Manual for Meeting the National Stormwater BMP Database Requirements, Apr. 25, 2002, 44 pgs.
Granato et al., "National Highway Runoff Water-Quality Data and Methodology Synthesis, vol. I—Technical Issues for Monitoring Highway Runoff and Urban Stormwater", U.S. Geological Survey, Publication No. FHWA-EP-03-054, Jul. 2003, 490 pgs.
Hutchinson et al., "Stormwater Monitoring Two Ecoroofs in Portland, Oregon, USA", Greening Rooftops for Sustainable Communities: Chicago 2003, 18 pgs.
Nieminen, "A Simple Device for Automatic Sampling of Runoff for Quality Monitoring During Rainfall Events", Boreal Environment Research, Jun. 19, 2000, vol. 5, pp. 133-136, ISSN: 1239-6095.
Nystrom, "Flow Proportional Sampling Techniques", The Ohio Water Environment Association, Jan. 23, 2014, Dayton, Ohio, 30 pgs.

* cited by examiner

SYSTEMS AND METHODS FOR WATER SAMPLING

FIELD OF THE INVENTION

The following description generally relates the collection an analysis of storm water runoff or outfall.

BACKGROUND

Storm water runoff can have a variety of effects on the environment as storm water runoff can bring with it many contaminants. Contaminants can have detrimental effects to crop growth and overall water usage. Furthermore, runoff can indicate erosion that is occurring. Thus it becomes useful to be able to collect run off samples and analyze the sample for contaminants.

Storm water runoff can vary from day to day and time of year. In some seasons runoff may be at peak levels in which it may be easy to collect samples from various runoff positions. On the other hand, it may be difficult to predict how much runoff may be present. As such, it may difficult to collect adequate samples during critical sampling times and to do so within a reasonable budget.

Current sampling methods have involved various sampling systems from simple manual grab sampling techniques as well as mechanical systems to fully automated systems. Manual sampling can pose dangers for the technician retrieving the sample because of the time required to obtain adequate samples after a storm and the potentially dangerous terrain associated with some sample locations. Timing to achieve desired hydrologic conditions to sample manually are also nearly impossible to predict and thus achieve. Therefore, more automatic mechanical systems have been developed for collecting samples. However, the cost and complexity limit the application of these techniques over space and continuation of monitoring stations overtime.

For example, some automatic systems can collect samples and then provide automatic feedback to remote locations. However, the complex systems have proven to be very expensive to purchase and operate, as well as ineffective at collecting adequate samples during various flow times. In order for water quality monitoring programs to be useful to inform the effectiveness water quality improvement solutions within the contributing drainages, stations need to be maintainable over many years. Cost of available complex systems is a barrier to long term stations. As previously discussed, the changing weather can affect the type and amount of runoff that is to be sampled. For example, in some manual systems only a single sample may be taken at certain flow levels. In other examples, where manual grab samples are performed, the sample is taken at a single point in time at a single location of the event flows from the storm. Extensive research has documented that storm runoff carries over 80% of the pollutant mass in the first 20% of the storm volume. Thus, the location on the hydrograph and the total flow at the time of sample collection has a significant influence on the concentration of the constituent within the sample obtained. As such it can become difficult to cost effectively obtain samples to provide an adequate picture of the quality of runoff sampled or the ability to obtain data to detect trends in the quality over time.

SUMMARY OF THE INVENTION

This invention generally relates to storm runoff systems in which many embodiments include a system for collecting fluid samples that has an external housing having at least six walls where the six walls are interconnected forming a housing with an internal chamber. The housing may be positioned in proximity of an external fluid source having at least one directional flow. Furthermore, the system has a plurality of elongated channels disposed within the internal chamber wherein, each of the plurality of channels has a first and a second end wherein each of the first and second end coordinate with opposite walls of the external housing and wherein each of the plurality of elongated channels further comprises a first opening at the first end such that a fluid may flow from the external fluid source into each of the plurality of channels, and wherein each of the plurality of elongate channels are disposed within the housing at differing levels. Additionally, the system has a plurality of elongated ducts with a first and a second end where the first end is in fluid communication with the external fluid source and wherein the second end of each of the plurality of ducts is in fluid communication with one of the plurality of elongated channels such that fluid may flow from the external fluid source into each of the elongated channels by way of the corresponding elongated duct. The system also has a plurality of sampling containers disposed within the plurality of elongated channels and configured to be in fluid communication with the fluid that enters each of the elongated channels such that a sample may be collected or distributed within each of the plurality of sampling containers. The system further comprised of a monitoring system configured to collect fluid flow data from the external fluid source and in electronic communication with a user receivable terminal, and a means for retrieving the plurality of sampling containers.

In other embodiments, at least a second opening is disposed at the second end of each of the plurality of elongated channels such that excessive fluid may drain from the channel during a collection process.

In yet other embodiments, a plurality of second openings are disposed at the second end of the elongated channels.

In still other embodiments, the means for retrieving the plurality of sampling containers comprises at least one access panel movably attached to at least one side of the external housing and having at least an open and a closed position.

In still yet other embodiments, the access panel further comprises a locking mechanism such that the access panel may be secured.

In other embodiments, the at least one access panel is hingedly attached to the external housing.

In yet other embodiments, the plurality of elongated ducts further comprise an angled portion at the first end and configured to be in fluid communication with the external fluid source such that the angled portion is positioned to be in contrast to the flow of the external fluid source.

In still other embodiments, a cap is disposed at the first end of each of the plurality of elongated ducts.

In still yet other embodiments, the cap further comprises a locking mechanism.

In other embodiments, a valve assembly is disposed within each of the elongated channels and configured to coordinate with the at least one opening at the first end of each of the elongated channels and wherein the valve assembly has at least an open and a closed position such that it may stop the flow of fluid into the elongated chambers at a desired time.

In yet other embodiments, the system further comprises a mechanism for opening and closing the valve assembly.

In still other embodiments, the mechanism for controlling the valve assembly is selected from a group consisting of a float and an electronic valve controller.

In still yet other embodiments, the plurality of elongated channels are configured within the housing such that the profile of the chambers resembles a stair like configuration or a staggered configuration.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which form a part of this disclosure.

BRIEF DESCRIPTION OF THE DRAWINGS

The description will be more fully understood with reference to the following figures, which are presented as various embodiments of the disclosure and should not be construed as a complete recitation of the scope of the disclosure, wherein.

DETAILED DESCRIPTION

The present disclosure may be understood by reference to the following detailed description, taken in conjunction with the drawings as described below. It is noted that, for purposes of illustrative clarity, certain elements in various drawings may not be drawn to scale.

The apparatus for sampling runoff water is described herein. In accordance with many embodiments, the apparatus described herein comprises a housing with a cavity wherein the housing is connected to a water runoff duct. A plurality of channels are disposed within the cavity that are designed to direct and capture runoff water from the duct at various stages of flow. The captured samples may be deposited into one or multiple containers. Once filled, the containers can be retrieved for evaluation and analysis.

Figure 1:
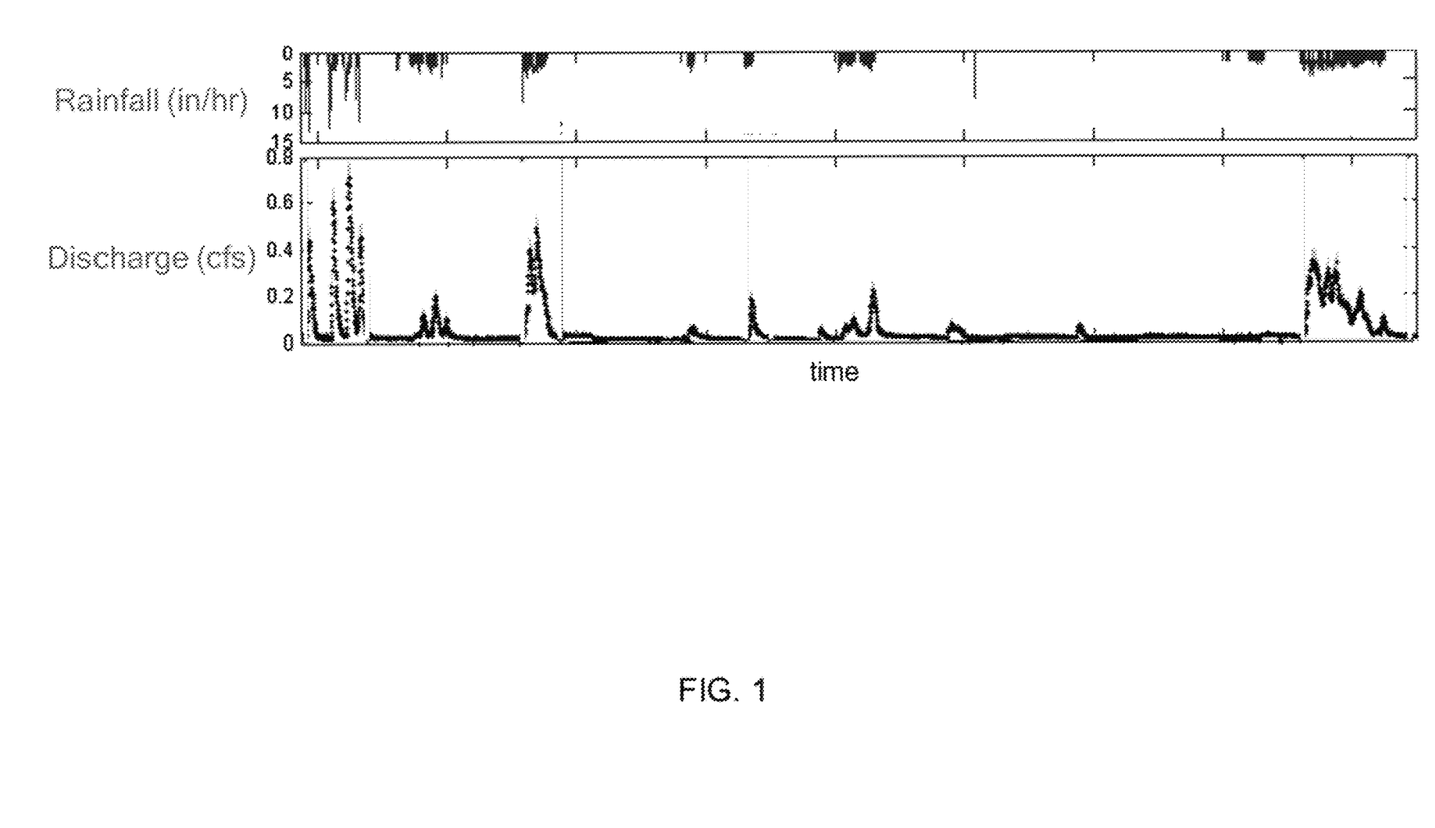
FIG. 1 is a graphical representation of rainfall vs. runoff discharge over time

In general, runoff amounts and flows can be difficult to predict as they are constantly changing with the changing environment as previously discussed. However, sampling of runoff flows can aid in the prediction of flow amounts and quality. As illustrated in FIG. 1, the runoff or discharge can be somewhat predicted based on the measured rainfall. This prediction is somewhat aided by sampling. However, manual sampling techniques can pose dangers to the technician as well as prove difficult to obtain adequate samples during critical runoff times. For example, manual samples require the technician to be on call and move quickly to sample locations to obtain the sample during the peak runoff. Urban and environmental conditions are continually changing and thus the samples only taken at peak runoff times may not provide accurate pictures of the runoff. Automated systems can help with these issues but have their own limitations.

Current automated systems typically incorporate a pump with a filter that is placed into or at the location of where the runoff is to occur. If the runoff is constant, then the pump location may be easily located within the flow of water. However, if runoff only occurs at peak times during storms or during certain seasons, the appropriate pump location may be difficult to ascertain. The pump systems may operate in such a way that when water is detected a signal is sent to the main unit to start collecting samples. These systems may not be completely accurate in obtaining a representative sample during the target flows. This is because the pump is located at a single position within the stream of water. For example, the extraction portion of the automated system may be typically placed in an outlet flow stream where the stream is relatively low during a low runoff time. That position will remain the same as flow increases during a storm or during a peak runoff season. As such, the sampling will only continue to sample the water from a specific point within the stream and may not necessarily provide an adequate sample of the overall flow rate or sediment content as flow increases. Systems such as these may require a larger number of samples to determine the content based analytical costs to determine pollutant concentrations and thus can lead to increased costs, not only for the machine but for the increased number of samples that require analysis as well. As such, the present invention described herein works to reduce the overall cost of implementation and analysis of runoff sampling.

Figure 2:
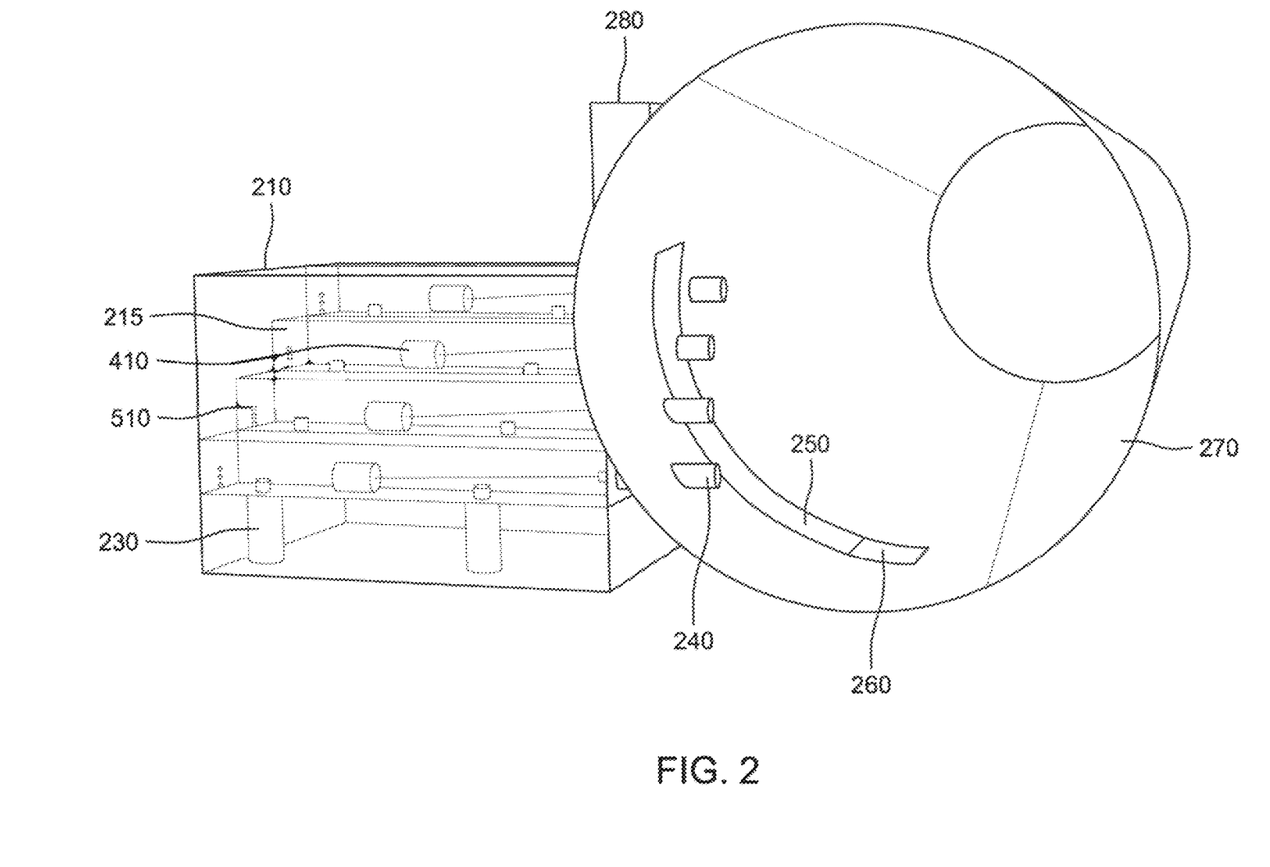
FIG. 2 illustrates a perspective view of an exemplary embodiment of the invention.

Turning now to FIG. 2 of the present invention, many embodiments of the water sampling system may include a structural housing 210 configured with any number of troughs or channels 215 located within the housing 210. In many embodiments, the troughs 215 may be configured with a plurality of sampling containers 230 to collect the water samples for further evaluation. Additionally, many embodiments may include a series of collection distribution ducts 240 that correspond to each of the troughs 215 within the housing 210.

Exemplary embodiments of the system are Illustrated in FIGS. 2-7 in which the water sampling system may further include data loggers 260 connected to a telemetry system 280 designed to collect and transmit data to an end user. Telemetry systems in accordance with many embodiments may include various components and will be discussed in further detail in subsequent sections.

Embodiments of the Housing

According to many embodiments, the housing may be configured in any number of ways. For example, in many embodiments the housing 210 may be directly or indirectly connected to the runoff channel 270. The housing 210 may be connected by any number of methods and may be supported in any number of ways such that the physical parameters of the housing do not create undue stress on the runoff channel 270. Regardless of the connection method, many embodiments will enable the housing to be in continuous fluid communication with the runoff channel 270.

Although not shown, in some embodiments the structural housing may be connected to the runoff channel by way of a separate mounting structure. The mounting plate may be mounted to the exterior surface of the runoff channel 270 and may be configured to interconnect with a corresponding portion of the structural housing 210.

In other embodiments, as can be illustrated in FIG. 2, the housing 210 may be located adjacent to the runoff channel 270 and indirectly connected to the channel by way of the collection distribution ducts 240. In such embodiments, the collection distribution ducts 240 enable the housing to be in fluid communication with the runoff channel 270; although, such embodiments do not place the housing in direct contact with the channel. Many embodiments may utilize any number of support structures to include an earth based structure that supports the housing 210.

Figure 3:
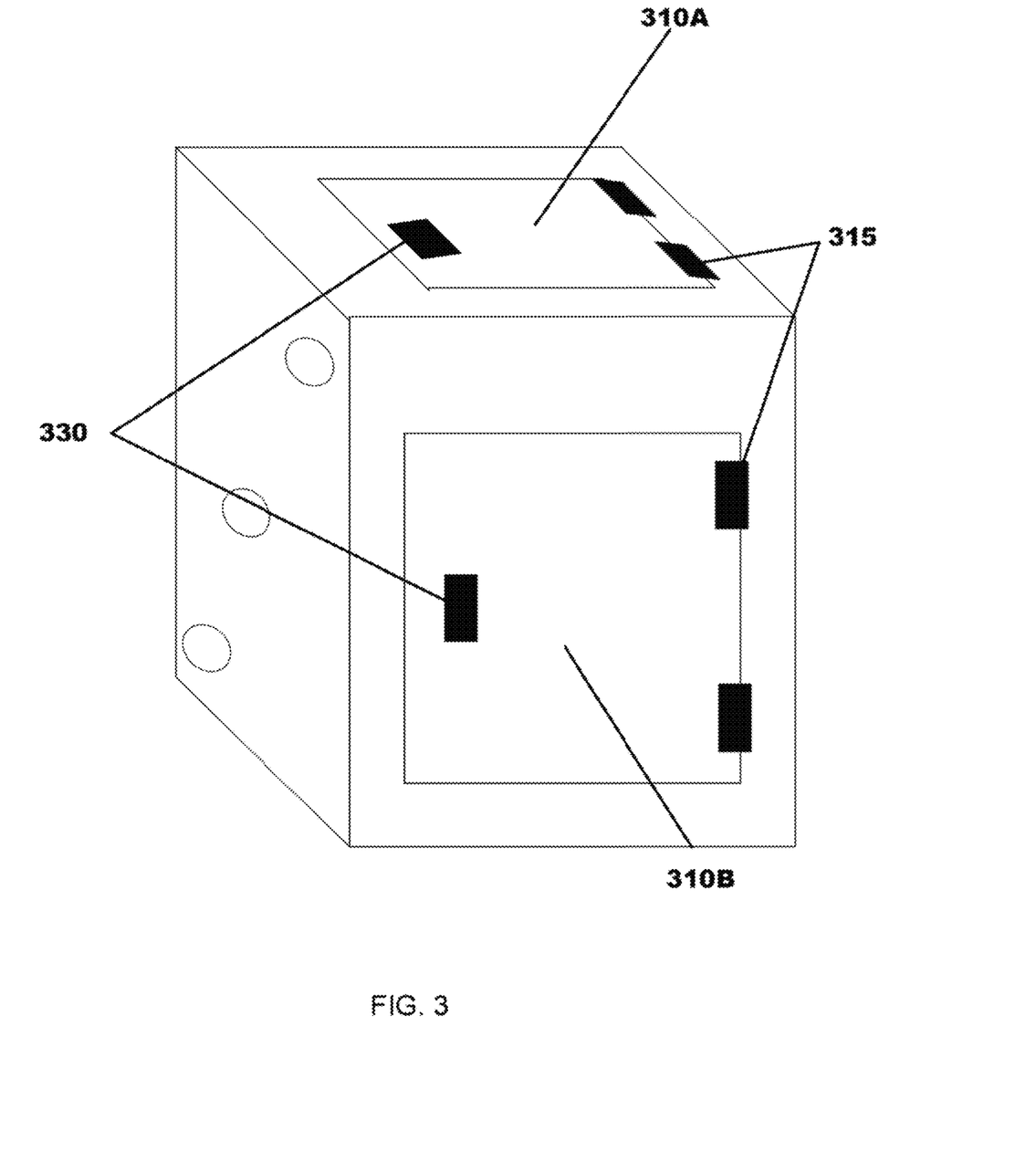
FIG. 3 illustrates a side view of an exemplary embodiment of the housing of the invention.

Turning to FIG. 3, many embodiments of the housing may include one or more access panels 310A and 310B. The access panels may be provided such that an end user may be able to perform maintenance on any number of components within the housing or the housing itself. Additionally, the access panels may provide a simple method to retrieve samples from the troughs 215 for further processing. In accordance with many embodiments, the access panels may be attached to the housing 210 in any number of ways. It is illustrated in FIG. 2 that the access panels 310A and B are attached via hinges 315 and further contain a handle 220 by which the access panel may be moved to access the interior of the housing. Although a specific method of attachment is shown it should be known that the access panel may be attached by any number of methods including a sliding mechanism, folding mechanism, etc. According to some embodiments of the invention, the access panel may comprise a single door or may comprise multiple doors. Any number of access panels and configurations may be sufficient based on the placement and ease of access desired for the given location. Although the housing is illustrated as a rectangular shape, it may take on any desired shape.

Embodiments of the Troughs

Figure 7:
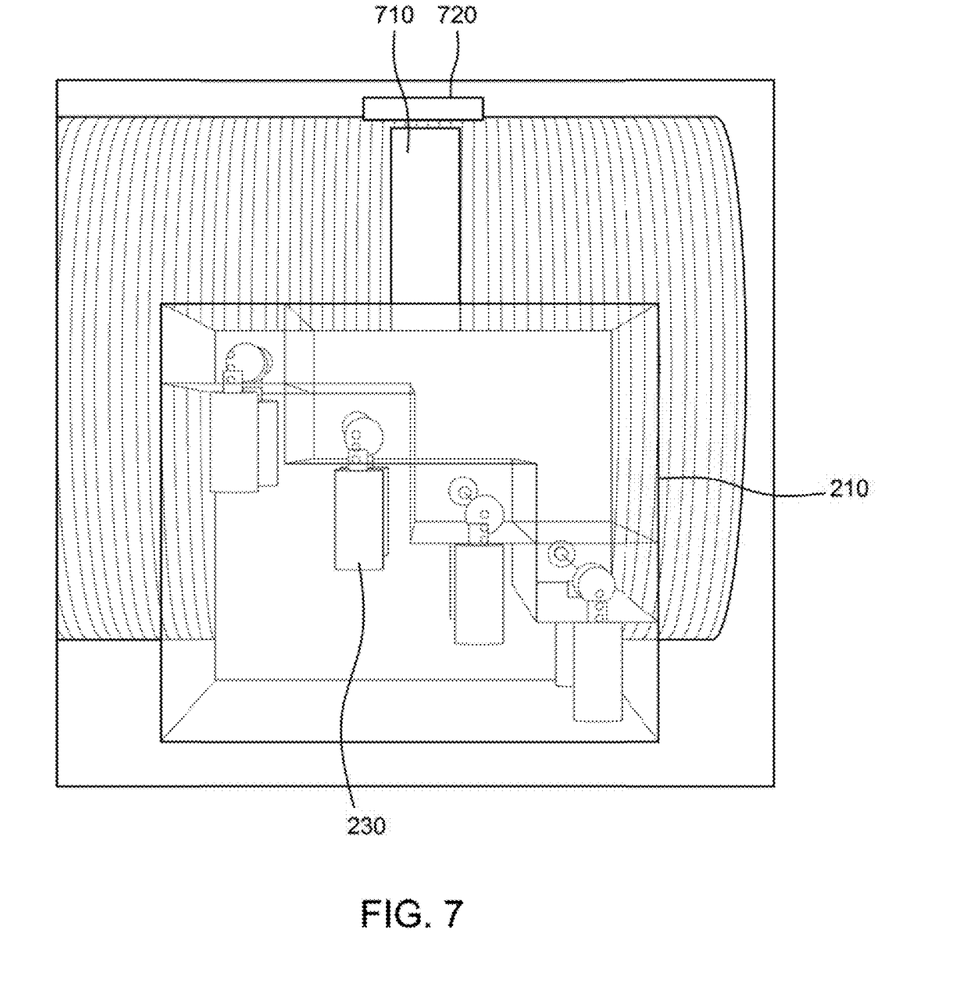
FIG. 7 illustrates another exemplary embodiment of the invention.

Turning now to the troughs 215, many embodiments of the system may include a number of troughs 215 disposed within the housing 210; as illustrated in FIGS. 2 and 7. According to many embodiments of the invention, the housing is configured with more than one collection trough 215 positioned at different heights. FIG. 2 illustrates an exemplary embodiment in which the collection troughs are staggered from the top to bottom and front to back of the housing creating a stair like profile.

The intent of the various levels is to account for the changing level of the flow such that the collection troughs 215 may be positioned to collect samples of water and debris in a manner that closely matches the change in the flow height and composition. The staggered positions, according to many embodiments, ensures the samples are taken from different points within the stream in coordination with the increasing flow. But that these points will always sample at the same flow as the flows increase within the stream or pipe. This ensures samples will be able to adequately measure how the flow and sediment changes over time rather than sampling at a single point within the pipe; which would require a greater number of samples to merely predict the flow and pollutant/constituent levels of the runoff. Although the embodiments illustrated in the figures show rectangular profiled collection troughs 215 it should be understood that the collection troughs 215 may take on any desired profile and configuration.

According to many embodiments, each of the collection troughs 215 may be configured to collect samples of water as it flows through the runoff pipe 270. Exemplary embodiments are illustrated in FIGS. 2, 4, and 7; where FIGS. 2 and 7 illustrate a profile configuration of the trough as it may be positioned within the housing 210.

Figure 4:
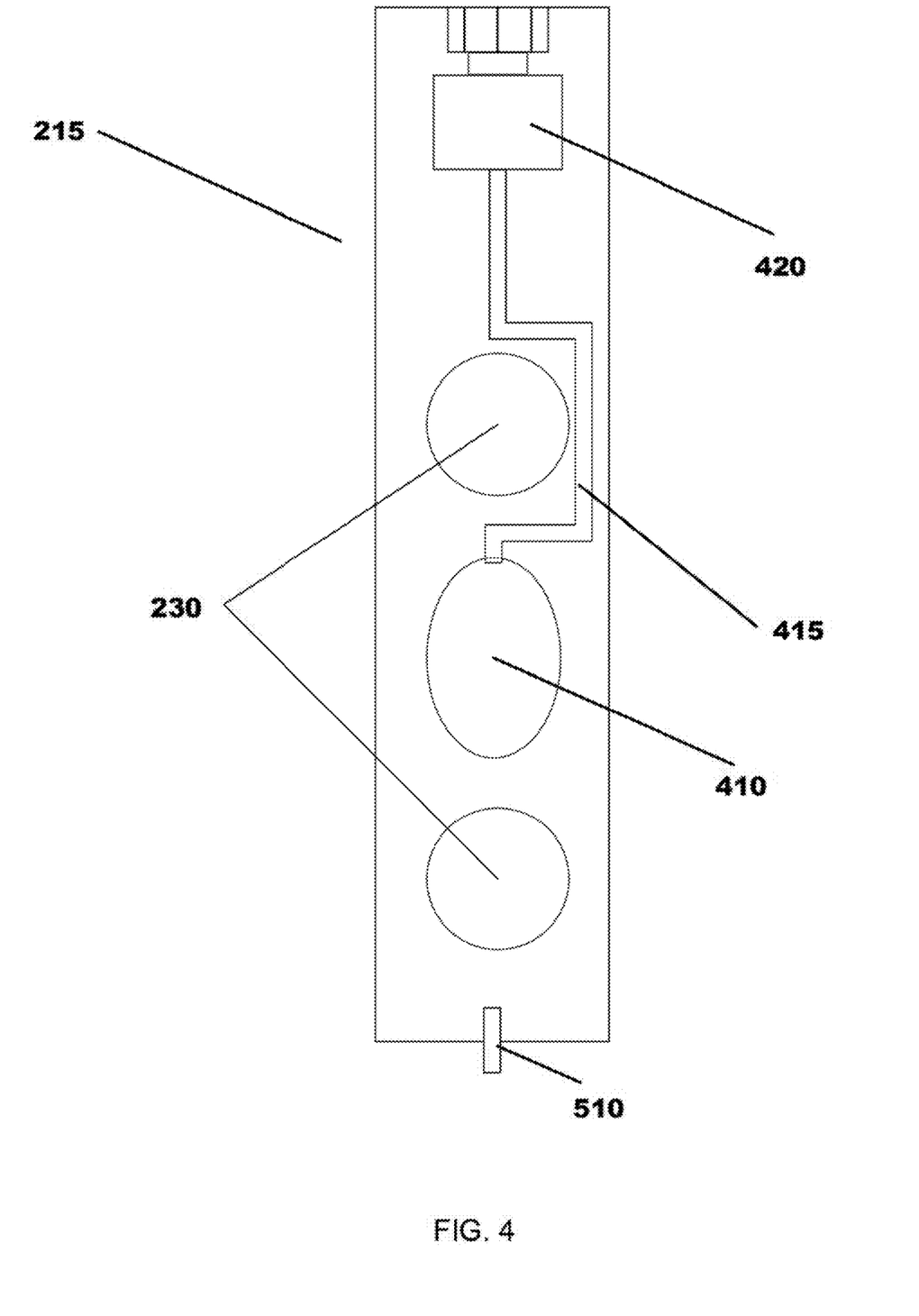
FIG. 4 illustrates an exemplary embodiment of a trough according to many embodiments of the invention.

Turning to FIG. 4, many embodiments of the trough 215 may comprise various components that assist in the collection of sample runoff water. For example, many embodiments may include a valve assembly 420 that may be configured to open and close as water from the runoff pipe 270 flows into the trough. In many embodiments, the valve assembly 420 may be equipped with a float stem 415 and a valve float 410. The valve float 410 and stem 415 may be configured to open and close the valve assembly 420 based on the water level within the trough 215. When no water is flowing through the runoff pipe 270 and subsequently no water is being captured within the trough, the float 410 may be at its lowest level and place the valve assembly in an open position. As the runoff water flow increases and water flows into the trough 215 the float 410 may raise until it closes the valve assembly 420. The valve assembly 420 may be in a closed position only when enough water is in the trough 215 such that the sample containers 230 have been filled. According to many embodiments, once the sample containers 230 have been filled, the containers seal and no more water may enter.

In many embodiments, the sample containers may be configured within the trough 215 such that the majority of the body of the container is located below the bottom surface of the trough 215. An exemplary embodiment of the trough 215 with sample containers 230 is illustrated in FIG. 5.

Figure 5:
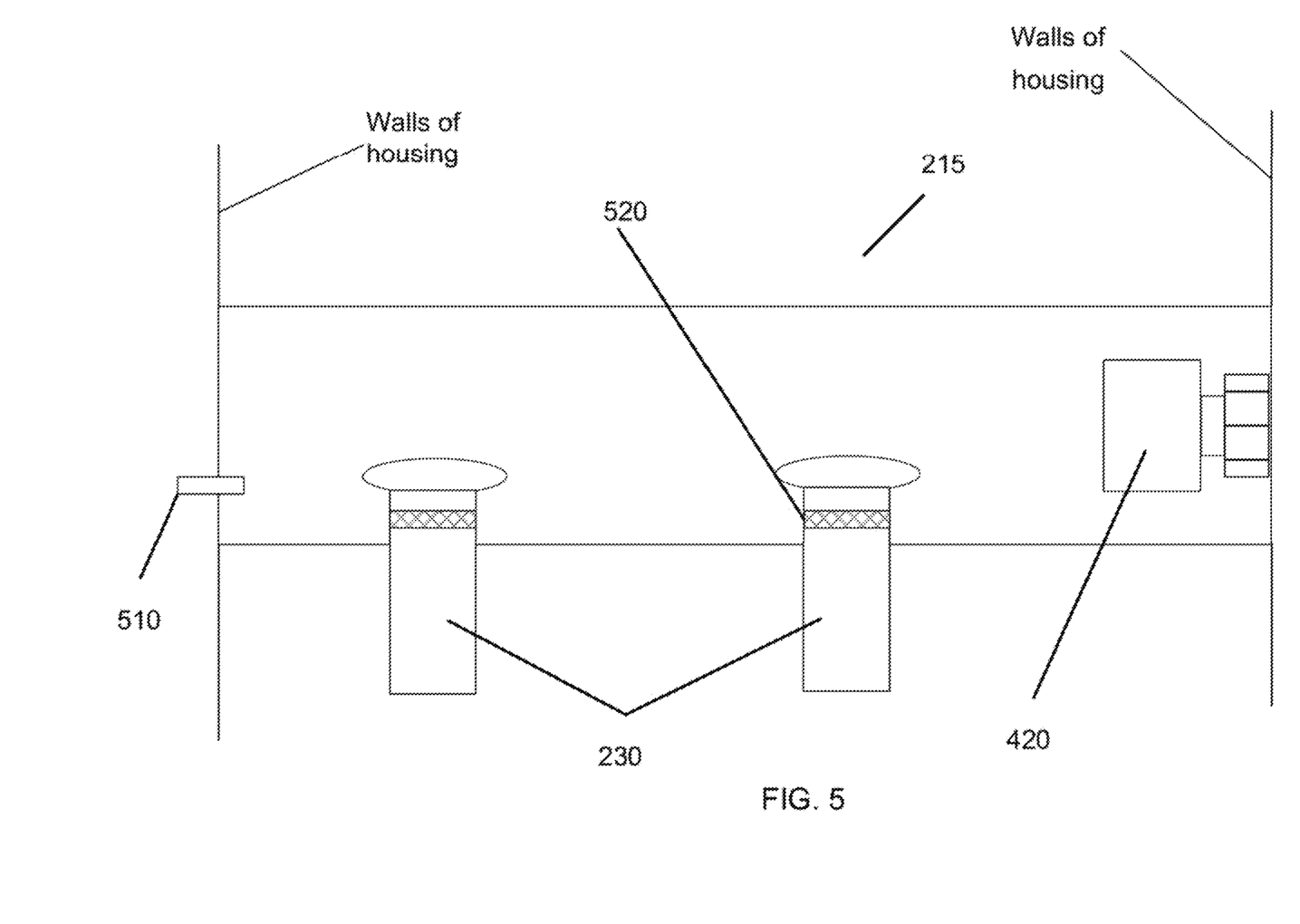
FIG. 5 illustrates a cross sectional view of various components according to many embodiments of the invention.

FIG. 5 illustrates a cross sectional front view of at least one of the troughs 215. It illustrates an exemplary embodiment in which the sample containers 230 are positioned within the body of the trough 215 such that the majority of the body of the sample container 230 is located below the body of the trough 215. This position will not require the trough to be completely filled in order to collect the necessary sample. Furthermore, more than one sample container 230 may be located within the trough 215 because, as the water flows, the composition may change. Therefore, the sample container(s) located further from the valve assembly 420 may have a different composition than the sample container(s) located closer to the valve assembly 420.

Each sample container 230, according to many embodiments of the invention, may be configured with a closeable opening 520 such that water from the runoff pipe may freely flow into the sample container 230 and when the container is full the container may be closed until it is prepared for additional testing.

Turning back to FIG. 2, troughs in accordance with many embodiments of the invention 215 may be configured to be positioned within the housing such that they extend the length of the housing. In other words, the side walls of the housing may act as the ends of the trough to hold in the water obtained from the runoff pipe.

Referring back to FIG. 5, in many embodiments, the ends of the troughs may be configured with weep holes 510. The weep holes 510 may be positioned on the wall of the housing that is located furthest from the run off pipe 270. Weep holes may be located at a desirable height within the trough and configured to allow water to escape the trough. The weep holes allow excess water to flow out of the trough after sample collection so that the end user may retrieve the sample containers 230 without being exposed to excessive amounts of runoff water. Weep holes can aid in the collection of samples after the runoff period. According to some embodiments, troughs may be configured with more than one weep hole. Although certain configurations are illustrated in the Figs., it should be understood that any preferable configuration may be used.

Embodiments of the Collection Distribution Ducts

As water flows in the runoff pipe, it can be desirable to direct or distribute the water for sampling from the pipe to the various troughs 215 located within the housing 210. According to many embodiments, the water collection system may be configured with a series of collection distribution ducts 240. Each of the collection distribution ducts 240 may correspond to an individual trough located inside the housing 210. It may be desirable to have more than one collection distribution duct 240 and it may be desirable to have one collection distribution duct correspond to multiple collection troughs 215.

In accordance with many embodiments, the collection distribution ducts may be configured to be in fluid communication with both the runoff pipe 270 and the collection troughs 215. Each collection distribution duct 240 must be the appropriate size for collecting water to ensure an adequate flow of water is drawn into the trough and distributed to the sample containers 230. As it can be desirable to draw in a sufficient amount of water for the sample containers 230, many embodiments may include an angled portion on the end of the collection distribution duct such than an opening of the duct is positioned to be within the flow of water in the runoff pipe. Furthermore, the angled portion may be configured such that the open end is facing upstream of the water flow. This allows for the natural flow of water to enter the ducts 240 without as much turbulence as might be occurring without the angled portion. In some embodiments the angle may change depending on the direction of the flow. The collection distribution ducts 240 may be configured in a variety of positions such that they redirect flow from the runoff pipe 270 into the collection troughs 215. According to many embodiments of the invention, the collection distribution ducts may be manufactured from a variety of materials such as any number of metals, plastic, PVC, etc.

Figure 6:
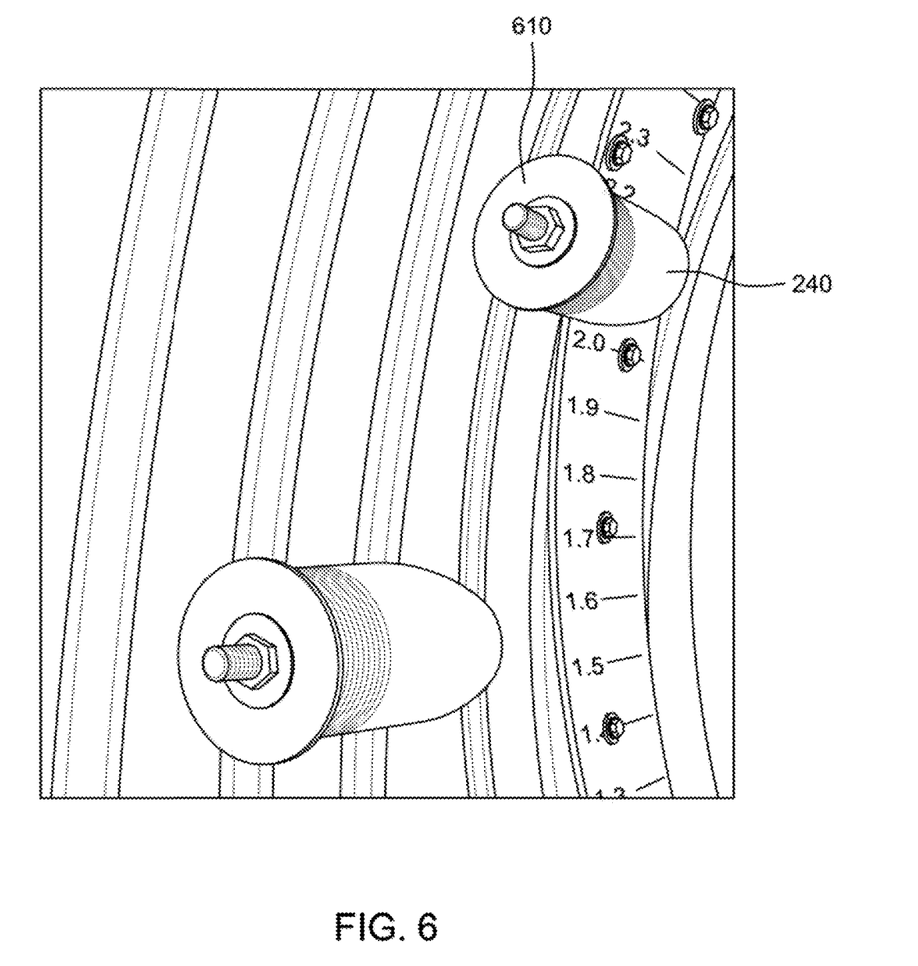
FIG. 6 illustrates an optional configuration in accordance with many embodiments of the invention.

Turning to FIG. 6, according to many embodiments of the invention, the opening of the collection distribution ducts may be configured with a removable cap 610. The removable cap may be desirable in the off season. In other words, when no flow is expected during a particular season or time of year, the removable cap 610 may be placed in the opening of the collection distribution duct 240 to prevent unwanted entrance. Although not shown, in accordance with some embodiments, the removable cap 610 may be configured with a keyed locking mechanism such that the cap may be locked in place until the peak runoff season is expected. The removable cap can aid in preventing small creatures such as birds or mice or insects from accessing and potentially damaging the distribution duct. Furthermore, it may act as a deterrent to other unwanted intruders.

Embodiments of the Telemetry System

In addition to the collection portion of the system, i.e. the collection troughs, ducts, and housing, many embodiments of the system may be configured with a telemetry communication system containing both a compartment for the data logger 260 and pipe for the wiring 250 and a housing unit that connects to the telemetry unit. The housing unit 250 is configured to protect the telemetry and data logger cable from damage from the water. Various proprietary data loggers exist on the market that can be programmed to measure and record water depth at defined intervals. Data loggers are placed at the bottom of the runoff pipe in a concealed compartment 260 to ensure consistent location and prevent theft or vandalism. A cable connects the data logger at the bottom of the pipe to the telemetry unit placed at a location where it will not be submerged and can receive adequate cell service, such as on top of the runoff pipe 270. Although not specifically shown, FIG. 2 illustrates an exemplary embodiment wherein the telemetry system 280 is configured to be in connection with the data logger within the runoff pipe 270. Although not readily shown in FIG. 2, the telemetry system 280, according to many embodiments, may be configured to receive flow data as the runoff water or flow increases. Data loggers record water depth which is transmitted via the telemetry unit to sampling personnel at an offsite location. Information from the data logger with water height from a runoff event can be used to discern water height in relation to collection troughs. In other words, using the telemetry unit, field personnel can monitor runoff events and sample collection from a remote location, thereby saving time and resources by not attending to the sampler following events that were not large enough to collect samples. The telemetry system may be used to communicate data from the flow of the runoff pipe 270 to a user preferably at a remote location. In accordance with many embodiments the telemetry system may be configured to be in electronic communication with a remote unit or a localized unit for transmitting data to an end user.

Another exemplary embodiment of a telemetry system is illustrated in FIG. 7. The wiring 250 may be housed in a separate wiring housing 710 that is located on the exterior of the trough housing 210. The telemetry unit may also be enclosed in a telemetry housing 720 that may be located on top of the runoff pipe, as illustrated in FIG. 7 or may be positioned in a separate location such as for example on top of the wiring housing 710. The telemetry system may take on any number of configurations depending on the geographical layout of the area and the positioning of the runoff pipe.

Figure 8A:
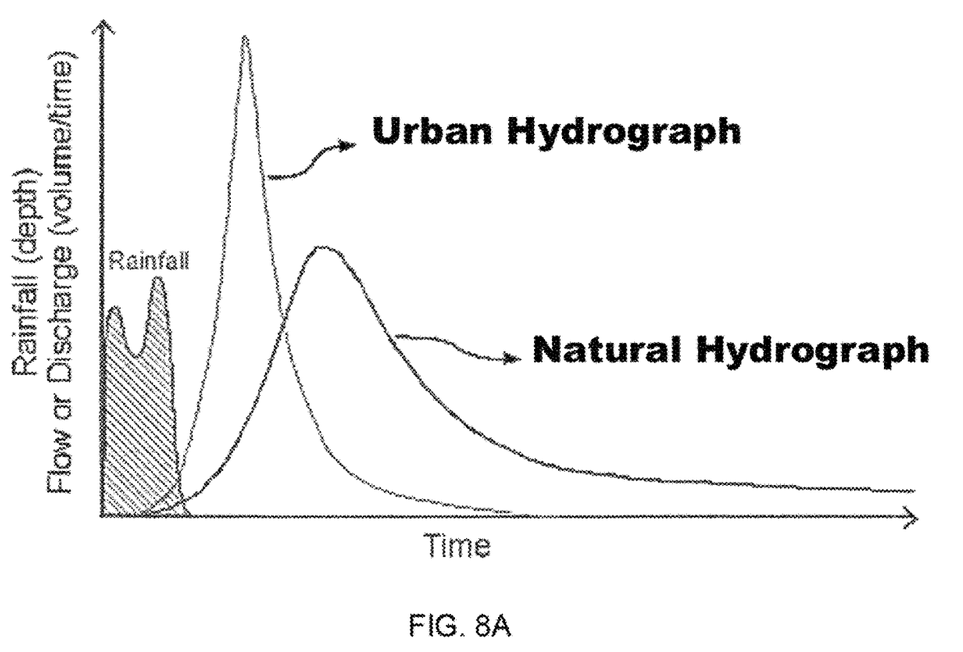
FIG. 8A illustrates a hydrograph comparison between urban and natural runoff. The exemplary embodiment is designed to obtain hydrologic and pollutant data to measure changes due to restoration of urban drainages and transition back to more natural hydrograph.
Figure 8B:
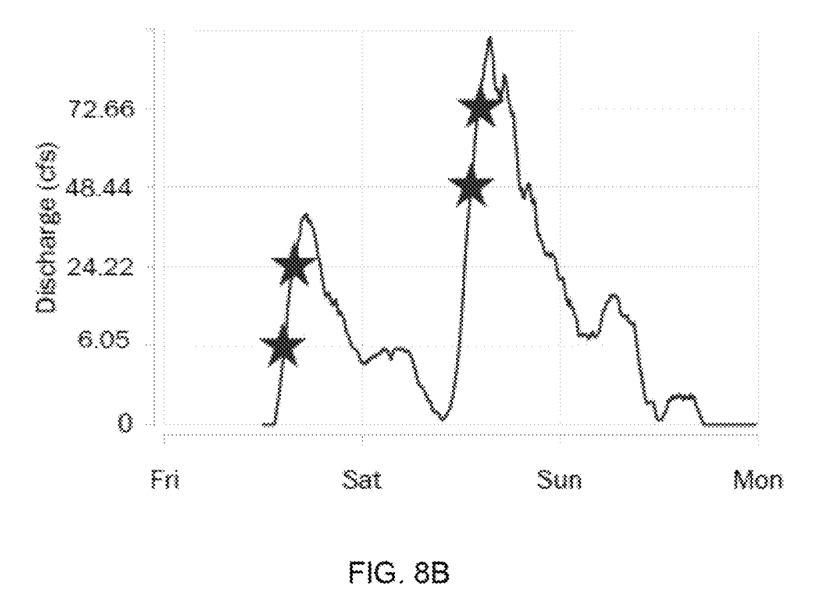
FIG. 8B illustrates the discrete discharge intervals where water samples are automatically collected at corresponding depths within a stormwater pipe by the exemplary embodiment.
Figure 9:
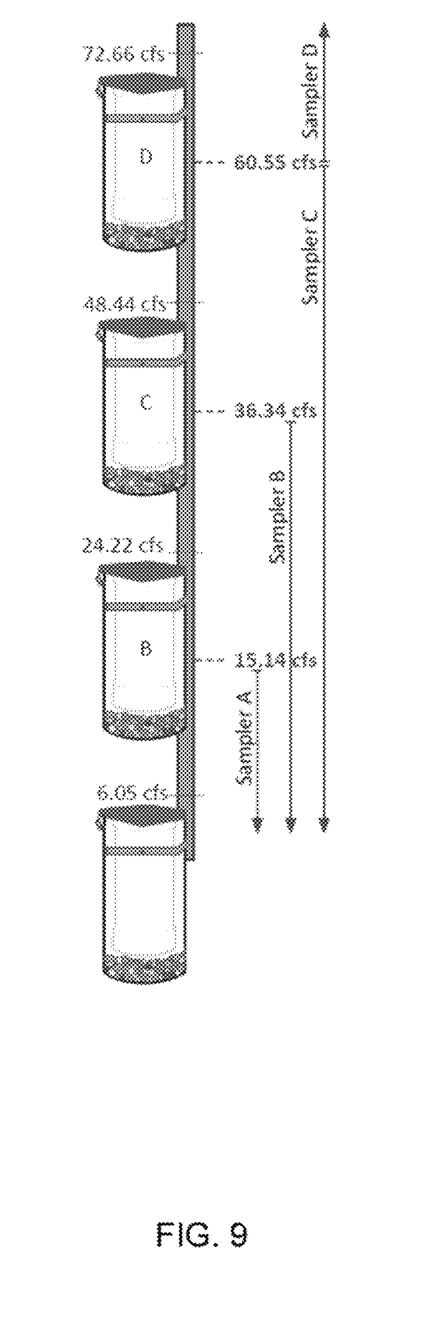
FIG. 9 is a vertical exaggeration of the how each sample bottle collects a discrete and unique water sample at distinct and consistent flows. The blue lines indicate how the sample constituent concentration results are applied to all sampled and unsampled flows within a defined range. The flow values are for illustration and vary for each site application of the invention.

FIGS. 8A 8B, and 9 illustrate various potential results of the collection system in accordance with many embodiments described herein. FIG. 8A illustrates hydrograph comparison between natural systems and urban systems in response to rainfall discharge over time. Stormwater capture, green infrastructure and other urban volume retention solutions intend to shift an urban drainage closer to a natural hydrograph. This system is designed to collect data to sample such a change. FIG. 8B illustrates the distinct sample collection for a hypothetical storm hydrograph. FIG. 9 is a vertical exaggeration of how water sample pollutant concentration results will be applied to all sampled and unsampled flows and distinct intervals based on the site specific configuration and flow conditions.

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. A system for collecting fluid samples comprising:
   an external housing having at least six walls wherein the at least six walls are interconnected forming a housing with an internal chamber located there between and positioned in proximity of an external fluid source having at least one directional flow,
   a plurality of elongated channels disposed within the internal chamber wherein, each of the plurality of channels has a first and a second end wherein each of the first and second end coordinate with opposite walls of the external housing and wherein each of the plurality of elongated channels further comprises a first opening at the first end such that a fluid may flow from the external fluid source into each of the plurality of channels, and wherein each of the plurality of elongated channels are disposed within the housing at differing heights,
   a plurality of elongated ducts having a first and a second end wherein the first end is in fluid communication with the external fluid source and wherein the second end of each of the plurality of ducts is in fluid communication with one of the plurality of elongated channels such that fluid may flow from the external fluid source into each of the elongated channels by way of the corresponding elongated duct,
   a plurality of sampling containers wherein each of the plurality of elongated channels are configured with at least one of the plurality of sampling containers and wherein each of the plurality of sampling containers are in fluid communication with the fluid that enters each of the elongated channels such that a sample may be collected or distributed within each of the plurality of sampling containers,
   a monitoring system that collects fluid flow data from the external fluid source and in electronic communication with a user receivable terminal, and
   a means for retrieving the plurality of sampling containers.

2. The system of claim 1 further comprising a second opening disposed at the second end of each of the plurality of elongated channels such that excessive fluid may drain from the channel during a collection process.

3. The system of claim 2 further comprising a plurality of second openings disposed at the second end of the elongated channels.

4. The system of claim 1, wherein the means for retrieving the plurality of sampling containers comprises at least one access panel movably attached to at least one side of the external housing and having at least an open and a closed position.

5. The system of claim 4, wherein the access panel further comprises a locking mechanism such that the access panel may be secured.

6. The system of claim 4, wherein the at least one access panel is hingedly attached to the external housing.

7. The system of claim 1, wherein each elongated duct of the plurality of elongated ducts further comprises an angled portion at the first end and is configured to be in fluid communication with the external fluid source such that the angled portion is positioned to be in contrast to the flow of the external fluid source.

8. The system of claim 1 further comprising a cap disposed at the first end of each of the plurality of elongated ducts.

9. The system of claim 8, wherein the cap further comprises a locking mechanism.

10. The system of claim 1 wherein each of the elongated channels further comprises a valve assembly cooperatively engaged with the at least one opening at the first end of an elongated channel and wherein the valve assembly has at least an open and a closed position such that it may control the flow of fluid into the elongated channel at a desired time.

11. The system of claim 10 further comprising a mechanism for controlling the valve assembly.

12. The system of claim 11, wherein the mechanism for controlling the valve assembly is selected from a group consisting of a float and an electronic valve controller.

13. The system of claim 1, wherein the plurality of elongated channels are configured within the housing such that the profile of the internal chamber resembles a stair like configuration or a staggered configuration.

* * * * *